United States Patent [19]

Giordano, Jr. et al.

[11] Patent Number: 4,606,326
[45] Date of Patent: Aug. 19, 1986

[54] IONICALLY POLYMER-BOUND TRANSITION METAL COMPLEX FOR PHOTOCHEMICAL CONVERSION OF LIGHT ENERGY

[75] Inventors: Paul J. Giordano, Jr., Hudson; Richard C. Smierciak, Streetsboro, both of Ohio

[73] Assignee: The Standard Oil Company, Cleveland, Ohio

[21] Appl. No.: 717,158

[22] Filed: Mar. 28, 1985

Related U.S. Application Data

[62] Division of Ser. No. 630,097, Jul. 12, 1984, Pat. No. 4,565,799.

[51] Int. Cl.$^4$ .............................................. B01J 31/08
[52] U.S. Cl. .................................... 126/400; 126/452; 502/155; 502/152
[58] Field of Search ...................... 204/158 R; 126/452, 126/400, 430, 900, 204; 432/1, 29; 502/163, 166, 167, 155, 152, 159; 165/2, DIG. 17

[56] References Cited

U.S. PATENT DOCUMENTS

| 2,950,237 | 8/1960 | Sharp | 204/158 R |
| 3,542,032 | 11/1970 | Spencer, Jr. | 126/204 |
| 4,004,571 | 1/1977 | Schwerzel et al. | 126/270 |
| 4,004,572 | 1/1977 | Nathan et al. | 126/270 |
| 4,004,573 | 1/1977 | Frieling et al. | 126/270 |
| 4,080,953 | 3/1978 | Mitchell et al. | 126/204 |
| 4,105,014 | 8/1978 | Schwerzel | 126/452 |
| 4,298,502 | 11/1981 | Carlson | 252/431 N |
| 4,378,305 | 3/1983 | Carlson | 252/431 N |
| 4,394,858 | 7/1983 | Giordano et al. | 204/158 R |
| 4,424,805 | 1/1984 | Neary | 126/452 |
| 4,446,041 | 5/1984 | Neary | 204/158 R |
| 4,449,516 | 5/1984 | Kitao et al. | 204/158 R |
| 4,504,371 | 3/1985 | Cirjak | 204/158 R |
| 4,507,185 | 3/1985 | King, Jr. et al. | 204/158 R |

FOREIGN PATENT DOCUMENTS 56-81137 7/1981 Japan.

OTHER PUBLICATIONS

J. Manassen, "Catalysis of a Symmetry Restricted Reaction by Transition Metal Complexes. The Importance of the Ligand", Journal of Catalysis (vol. 18, 38-45, 1970).

L. D. Rollman, "Porous, Polymer-Bonded Metalloporphyrins", Journal of the American Chemical Society, (vol. 97, 2132-2136, 1973).

B. B. King et al., "Polymer-Anchored Cobalt Tetraarylporphyrin Catalysts of Quadricyclane to Norbornadiene", Journal of Organic Chemistry, (vol. 44, No. 3; 385-391, 1979).

K. Maruyama et al., "Exploitation of Solar Energy Storage Systems. Valence Isomerization Between Norbornadiene and Quadricyclane Derivatives", Journal of Organic Chemistry (vol. 46, 5294-5300, 1981).

Primary Examiner—Samuel Scott
Assistant Examiner—H. A. Odar
Attorney, Agent, or Firm—Sue E. McKinney; Joseph G. Curatolo; Larry W. Evans

[57] ABSTRACT

Novel catalyst for the photochemical conversion and storage of radiant energy through the conversion of strained cyclic non-conjugated carbon containing compounds to their corresponding conjugated forms comprises ionically bonding a transition metal complex having a square planar geometry and multiple sites of coordination with an anion-exchange resin. A method is provided for the preparation of the novel catalyst and comprises forming an acid salt derivative of the transition metal complex and mixing it together with an anion-exchange resin. A process wherein the novel catalyst is added to a strained cyclic non-conjugated carbon containing compound resulting in the release of heat energy through the conversion of the non-conjugated carbon containing compound to its conjugated form. A process and sealed container means wherein the non-conjugated carbon containing compound and the catalyst are in compartments and are separated until heat energy is required. The means of separation is then broken and the non-conjugated carbon containing compound is converted to the conjugated form with the release of heat energy. A process and apparatus wherein the conjugated carbon containing compound is exposed to radiant energy and is converted to the non-conjugated form. The non-conjugated form is then combined with the catalyst described hereinabove, converting the non-conjugated form to the conjugated form and resulting in the release of heat energy which is collected.

22 Claims, 1 Drawing Figure

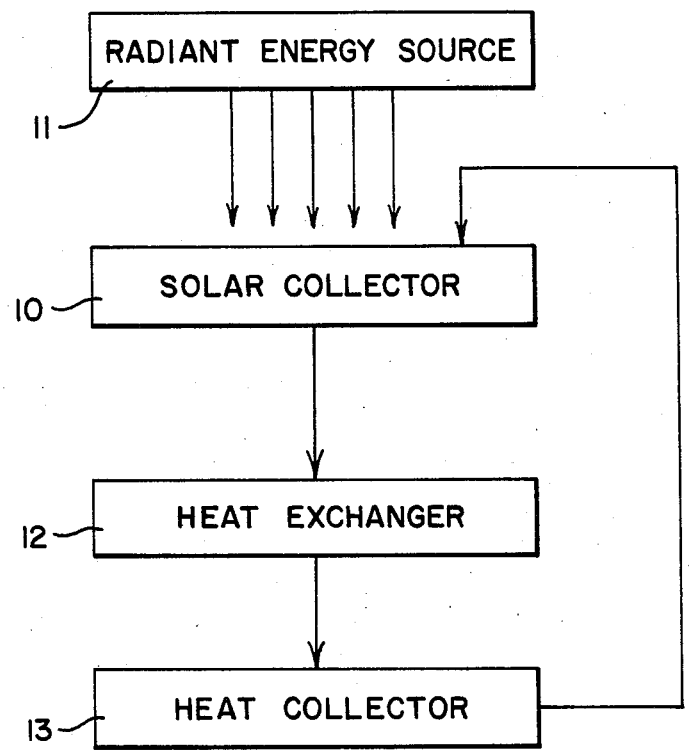

IONICALLY POLYMER-BOUND TRANSITION METAL COMPLEX FOR PHOTOCHEMICAL CONVERSION OF LIGHT ENERGY

This application is a division of application Ser. No. 630,097, filed July 12, 1984, now U.S. Pat. No. 4,565,799.

TECHNICAL FIELD

The present invention is directed toward a catalyst which can be employed in the photochemical conversion of light energy. The catalyst comprises a transition metal complex bound to a polymer ionically. The catalyst is specifically utilized to convert strained cyclic non-conjugated carbon containing compounds to their corresponding conjugated forms.

The present invention is also directed toward a method for the preparation of the abovementioned catalyst. And finally, the present invention is directed toward various processes and apparatus for the conversion of strained cyclic non-conjugated carbon containing compounds to their corresponding conjugated forms which employ the subject catalyst.

BACKGROUND ART

U.S. Pat. Nos. 4,004,571, 4,004,572 and 4,004,573 disclose the solar energy induced isomerization of organic isomerizable compound to a high energy intramolecular strained ring structure. It is stated that such isomerizations may be aided by photosensitizers which absorb light in the visible wavelengths and then transfer energy to the isomerizable compound to induce the isomerization reaction to occur. The high energy isomer stores the solar energy in the strained ring structure until induced by heat or catalysis to revert to its lower energy isomeric form. The stored energy is released during the reverse isomerization in the form of heat energy. Various suitable isomerizable compounds and energy release (reverse isomerization) catalysts are listed in these patents, the disclosure of which is hereby incorporated by reference, as if written out in full, in the application.

The use of various unbound transition metal complexes to convert strained cyclic non-conjugated olefins is known in the art. A journal article by Manassen entitled "Catalysis of Symmetry Restricted Reaction By Transition Metal Complexes. The Importance of the Ligand" appearing in the *Journal of Catalysis* (1970) discloses the use of square planar transition metal complexes in the valence isomerization of quadricyclane to norbornadiene.

The specific conversion of a high energy quadricyclane derivative to the corresponding norbornadiene from has been disclosed by Maruyama et al in a journal article entitled "Exploitation of Solar Energy Storage Systems Valence Isomerization between Norbornadiene and Quadricyclane Derivatives" appearing in the *Journal of Organic Chemistry* (1981). The reaction is thermal and is done in benzene at 80° C. for five hours.

The covalent bonding of transition metal complexes to polymers is also known. A journal article by Rollmann entitled "Porous, Polymer-Bonded Metalloporphyrins" appearing in the *Journal of the American Chemical Society* (1975) discloses different techniques for bonding porphyrins to porous polystyrene resins. The linkages utilized are covalent bonds and include amine, ester, ketone, and alkyl linkages.

A jounral article by King et al entitled "Polymer-Anchored Cobalt Tetraarylporphyrin Catalysts for the Conversion of Quadricyclane to Norbornadiene" appearing in the *Journal of Organic Chemistry* (1979) discloses a complex scheme for bonding a cobalt tetraarylporphyrin catalyst to macroreticular polystyrene beads with covalent bonds.

Thus, while the art provides various catalysts for the conversion of strained cyclic non-conjugated carbon containing compounds to their corresponding conjugated forms, and the art also provides for the covalent bonding of various catalysts onto polymers, the art has not disclosed the subject transition metal complexes bound to a polymer ionically. Furthermore, a method for the preparation of this catalyst and various processes and apparatus employing it have also not been disclosed.

SUMMARY OF THE INVENTION

In general, the catalyst of the subject invention, which can be employed in the photochemical conversion and storage of light energy through the conversion of strained cyclic non-conjugated carbon containing compounds to their corresponding conjugated forms, comprises a transition metal complex having a square planar geometry and multiple sites of coordination, and which is bound ionically to a polymer which is an anion-exchange resin. The square planar geometry and multiple sites of coordination are provided for by a complex chosen from the group consisting of porphyrins, phthalocyanines and macrocyclic tetraaza complexes.

The method of preparing the catalyst comprises the steps of forming an acid salt derivative of the transition metal complex; dissolving it in water; and, mixing in an anion-exchange resin to yield an ionically polymer-bound transition metal complex.

A process for the conversion of a strained cyclic non-conjugated carbon containing compound to its corresponding conjugated form comprises the steps of adding the abovementioned catalyst to the non-conjugated carbon containing compound; and, converting it to its conjugated form with the release of heat energy.

The subject invention also provides a process and a container wherein the strained cyclic non-conjugated compound and the catalyst are in separate compartments until heat is necessary, at which time a frangible means of separation is broken. This results in the catalyst and the non-conjugated carbon containing compound interacting and the latter being converted to the conjugated form with the release of the desired heat energy.

Finally, the subject invention provides a process and an apparatus for the photochemical conversion and storage of radiant energy which utilizes the exposure of the strained cyclic conjugated carbon containing compound to radiant energy which results in the conversion to the non-conjugated form. This non-conjugated form is then reacted with the subject catalyst which is coated on a heat exchanger. The non-conjugated form either can be transported to the coated heat exchanger or the heat exchanger can be immersed into the non-conjugated form. Either process results in the conversion of the non-conjugated form back to the conjugated form and the release of heat energy.

PREFERRED EMBODIMENT FOR CARRYING OUT THE INVENTION

An important feature of the present invention is the photochemical conversion of a strained cyclic non-conjugated carbon containing compound to its conjugated form. This conversion results in the release of potential energy in the form of heat, and thus can provide a useful application of solar or light energy. Until the conversion, however, the potential energy derived from the light energy can be stored as the conjugated form with minimal dissipation.

The basis of the abovementioned release of energy and of all photochemical reactions is that activation of a molecule is provided by absorption of a photon of light to produce an electronically excited state, separated from the ground state by discrete energy levels. Only light absorbed by a system is effective in producing a photochemical change, and each photon or quantum of light absorbed or "captured" activates one molecule in the primary excitation step of a photochemical sequence. Each photon or quantum absorbed by a molecule has a certain probability of activating an electron to either the lowest excited singlet state, or the lowest excited triplet state, which states are required to initiate essentially all photochemical processes.

The energy difference between the excited state of a molecule and the ground state of the molecule, on a mole basis, is the activation energy for that molecule, measured in kilocalories per mole. The activation energy may be referred to as the triplet energy.

This activation energy or triplet energy may be released by several processes. The molecule may relax to the ground state after activation by releasing energy by the emission of light. More importantly, the activated molecule may release the energy of activation by transferring the energy to another molecule, thereby raising the energy level of the second molecule to an excited state and being "quenched" by it.

BRIEF DESCRIPTION OF THE DRAWING

The drawing FIGURE depicts schematically one form of apparatus for the storage and conversion of radiant energy employing a catalyst of the subject invention.

The quenching molecule may itself release the activation energy, or the activation energy may overcome an energy barrier in the molecule to allow a chemical or structural transformation to occur. An example of this would be the isomerization of a molecule to a higher energy or a less sterically favored conformation. If the high energy conformation is stable, the energy of activation, or some increment of that energy, is stored in the molecule by virtue of the potential energy represented by the high energy conformation.

The organic compounds to which this invention is applicable have significant storage enthalpies, due to the creation of bond angle strain in small, intramolecular, carbon containing rings or due to the loss of resonance in pi bonding systems. The photoisomerized product is thermodynamically unstable, but orbital topology constraints or symmetry restraints confer kinetic stability which inhibits the reverse reaction so that the energy represented by the potential energy difference between the isomers can be stored. This energy is releasable upon the reverse isomerization of the molecule to a more sterically favored conformation after overcoming the kinetic stability either thermally or catalytically.

In order to drive the photoisomerization reaction, according to classical excited state electronic energy transfer theory, the photocatalyst should have an activation energy, or lowest excited state (triplet) energy that is greater than the energy required to excite the quencher molecule to the state required for the isomerization to occur.

Strained cyclic non-conjugated carbon containing compounds suitable for use in the practice of the present invention are those which can quench the triplet energy state of photosensitizers to effect a reversible intramolecular isomerization to a high energy conformation. The compounds preferably include in their molecular structure at least two reactive carbon to carbon double bonds. Using the preferred compounds, the photocatalyst quenching reaction is accompanied by an intramolecular cyclization of the isomerizable compound to form a strained ring structure in which the potential energy is stored, and is released with the subsequent addition of the subject catalyst.

These strained ring structures are preferred for the capture and storage of light energy because the conjugated form of the strained cyclic carbon containing compound has pi-bond symmetry which will convert to its corresponding non-conjugated form having sigma-bond symmetry easily in the presence of light energy. However, the reverse conversion will not occur spontaneously because there is a large energy of activation due to orbital constraints. The non-conjugated form is indefinitely stable at room temperature because its orbitals are symmetrically forbidden to go from sigma-bond symmetry to pi-bond symmetry.

Exemplary strained cyclic non-conjugated carbon containing compounds include quadricyclane, cyclopentane, cubane, dibenzotricylooctadiene, anti-tricyclooctene, hexamethyl dewar benzene, tricyclo$[2.2.0.0^{2,6}]$hexane and functional derivatives thereof. Preferred derivatives include carboxylic acid groups and esters groups having up to about 3 carbon atoms each. Other suitable compounds are described in U.S. Pat. Nos. 4,004,571, 4,004,572 and 4,004,573. The foregoing description and disclosure of carbon containing compounds are meant to be illustrative of the strained cyclic non-conjugated carbon containing compounds which can be converted by the subject catalyst but should not be construed as exhaustive or limiting.

The transition metal complex must have certain characteristics. First, the strained cyclic non-conjugated carbon containing compound must be able to react with the metal electronic orbitals of the catalyst. Second, the metal electronic orbitals need to be perpendicular to each other since the sigma-orbitals of the non-conjugated form are perpendicular to the pi-orbitals of the conjugated form. Third, the metal electronic orbitals must be close in energy to each other. Finally, one set of metal electronic orbitals must be vacant to allow room for a ligand donor such as the strained cyclic non-conjugated carbon containing compound to enter and bind to the metal orbitals.

The complex that has these characteristics is a square planar compound having multiple sites of coordination. A square planar compound has vacant sites for the entering non-conjugated carbon containing compound since there are only four ligands in the coordination sphere as compared to six ligands of an octahedral complex. Also, the metal orbitals of a square planar complex are much closer in energy as compared to an octahedral complex. Finally, typical transition metals have six, seven, or eight d-electrons and a complex thereof will have vacant orbitals to allow room to accept electron density from an entering ligand donor.

An example of a specific square planar transition metal complex is a metalloporphyrin which has the following structure:

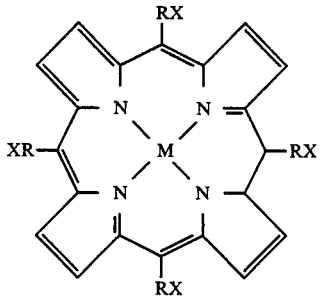

wherein M is a transition metal, R is selected from the group consisting of phenyl, alkyl, cycloaliphatic, unsaturated t-butyl, and x is selected from the group of H, —COONa, —SO$_3$Na, —COOK, —SO$_3$K, —COONH$_4$ and —SO$_3$NH$_4$. A specific example wherein M is cobalt and R is phenyl is cobalt (II) meso-tetraphenyl porphyrin.

Another example of a square planar transition metal complex is a metal phthalocyanine complex which has the following structure:

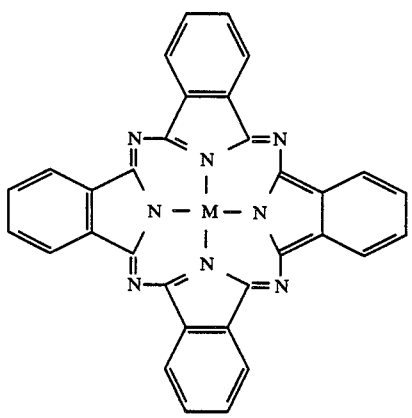

wherein M is a transition metal.

Another example is a metal macrocyclic tetraaza complex which has the following structure:

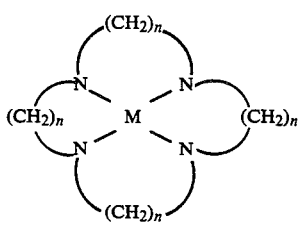

wherein M is a transition metal and n is between 1 and about 20.

Other examples of specific compounds having square planar geometry include chloronorbornadiene rhodium (I) dimer, tris(dimethylphenylphosphine)norbornadiene rhodium (I) hexafluorophosphate, chlorobis(ethylene)rhodium (I) dimer, dichloro(1,5-cyclooctadiene)palladium (II) and chlorodicarbonyl rhodium (I) dimer.

The polymer to which the transition metal is bound is an anion-exchange resin. The resin must be strongly basic and capable of being separated quantitatively from the transition metal. Suitable examples of these resins include polystyrene divinylbenzene macroporous crosslinked resin of which Amberlyst A-26, manufactured by Rohm and Haas is an example. Unexpectedly, the transition metal complex can also be "loaded" onto the anion-exchange resin by adjusting the stoichiometric ratio of the complex to the resin. If the ration is high, intense heat for brief periods can be realized; if the ratio is low, moderate heat for extended periods is realized, and thus can effectively control the rate of heat released.

The catalyst is prepared by forming an acid salt derivative of the transition metal complex. The acid salt derivative is typically a combination of a salt chosen from the group consisting of sodium, potassium, lithium, magnesium, calcium and ammonium salts and the sulfonic acid or carboxylic acid derivative of the complex. This acid salt derivative is then dissolved in water and subsequently added to the anion-exchange resin and stirred. The polymer-bound transition metal complex is then dried utilizing a solvent and ambient temperature. The complex is now rigidly held by the polymer and could be physically removed quantitatively from the non-conjugated carbon containing compound in solution by filtration. This overall method is much simpler than the complicated procedures disclosed in the art for covalently bonding the transition metal complex.

The catalyst thus formed can then be employed in a process wherein the catalyst is added to the non-conjugated carbon containing compound in solution; converting the non-conjugated form to its corresponding conjugated form with the release of heat; removing the catalyst from the conjugated carbon containing compound by filtration; and exposing the conjugated form to radiant energy to reconvert it to its original non-conjugated form. This process can be performed once or the catalyst can be re-added to the non-conjugated form. Also the additional step of regenerating the catalyst may be performed by removing the transition metal complex from the polymer by using a brine solution, and then adding a new portion of the transition metal complex to the "cleaned" polymer. In this way, if the activity of the catalyst should decrease through recycling, the resin can still be reused by adding a new or reactivated portion of the transition metal complex.

The subject catalyst and process can practically be employed as an instant source of heat wherein the strained cyclic non-conjugated carbon containing compound and the subject catalyst are contained and stored in separate compartments until a source of heat is required. At that time, the barrier between compartments is physically broken to allow the non-conjugated compound and the catalyst to mix, causing the non-conjugated compound to convert to its conjugated form and the release of heat to occur. The stoichiometric ratio of the complex to the resin of the catalyst could be altered depending on the intensity of heat desired. This chemical heat source is particularly applicable to situations wherein the use of flame heat is prohibitive or impossible.

Another practical use of the subject catalyst and process is as part of a solar energy heating system. The solar energy can be collected by exposing the conjugated form of the strain cyclic carbon containing compound to light resulting in its conversion to its non-conjugated form. The non-conjugated form can then be collected and stored until heat is desired. At that time, the non-conjugated form can be passed through a heat exchanger coated with the subject catalyst resulting in the conversion of the non-conjugated form back to its conjugated form and resulting in the release of heat which is collected. The rate of heat can be altered by the concentration of the coating of the catalyst on the heat exchanger.

With reference to the drawing, an apparatus for the photochemical conversion and storage of radiant energy is depicted schematically. First, a container or solar collector 10 is provided for a strained cyclic conjugated carbon containing compound. The compound is there exposed to a radiant energy source 11 such as sunlight or other uv source. As a result of the exposure, the compound is converted to a strained cyclic non-conjugated carbon containing compound.

When heat is desired, the strained cyclic non-conjugated carbon containing compound is passed through a heat exchanger 12 that has been coated with the catalyst of the present invention. The catalyst converts the non-conjugated form back to the conjugated form with the release of heat, collected in heat collector 13. The conjugated form is then returned to the solar collector 10 for repeat of the cycle.

The following example demonstrates the practice of the present invention. It is to be understood that this example is utilized merely for illustrative purposes and is not to be considered a limitation of the invention.

EXAMPLE 1

First the acid salt derivative of a square planar transition metal complex was prepared by charging a flask with 2.0 g tetrasodium-meso-tetra(4-sulfonatophenyl porphyrin) (12-hydrate) and 50 ml of N,N-dimethylformamide (DMF). The resulting solution was purple, to which 0.35 g of cobalt (II) dichloride hexahydrate dissolved in 50 ml of DMF was added. It is to be noted that the DMF was employed as a solvent to get both cobalt compounds into solution. The reaction mixture was allowed to reflux and the DMF was removed yielding a sample of cobalt (II) tetrasodium mesotetra(4-sulfonatophenyl)porphyrin. A solution containing 1 g of this and 25 ml of distilled water was then prepared. Separately, a 5 g sample of a strongly basic anion-exchange resin, Amberlyst A-26, was obtained and was washed to remove any manufacturer residue. The specific resin employed is a polystyrene divinylbenzenc macroporous cross-linked resin. The transition metal complex solution was poured onto the resin and stirred. The resulting filtrate was colorless indicating all the transition metal complex had been exchanged onto the resin. The polymer-bound complex was then washed and dried at ambient temperature.

The catalyst was then tested by adding it to a solution of quadricyclane, which is a typical strained cyclic non-conjugated olefin, and measuring the percent conversion to its corresponding conjugated form, norbornadiene. The conversion was measured over time and is reported in Table I.

TABLE I

| | Conversion of Quadricyclane to Norbornadiene by a Polymer-Bound Cobalt (II) Porphyrin | | |
|---|---|---|---|
| Time(hr) | % Q | % NBD | % Accounted For |
| 0.0 | 99 | 1 | 100 |
| 0.1 | 97 | 3 | 100 |
| 0.3 | 94 | 6 | 100 |
| 18.9 | 51 | 49 | 100 |
| 19.7 | 48 | 52 | 100 |
| 21.8 | 45 | 55 | 100 |
| 22.4 | 40 | 60 | 100 |
| 40.0 | 2 | 97 | 99 |

Based upon the results of Table I it can be seen that the polymer-bound transition metal complex results in a high percent of conversion. Based on these results, it is feasible to cycle a chemically reversible energy system 100 times. This is important inasmuch as one would need to recycle the process many times to reduce costs to a level competitive with existing gas or electric heating systems. Also this high percent of conversion is an improvement over the art inasmuch as the art typically discloses percents of conversion only in the 90 to 94 percent ranges.

Thus, it should be apparent to those skilled in the art, that the subject invention provides a novel catalyst, a method for the preparation thereof and a process employing it. Furthermore, the combination of the subject square planar transition metal complex and an anion-exchange resin unexpectedly is much easier to make and use as compared to the existing catalysts employing covalent bonding. Specifically, the method of preparation of the catalyst has fewer steps, and the use of the catalyst in a process has the advantages of being able to effectively control the release of heat by "loading" the catalyst and of being able to recycle the catalyst many times.

It is to be understood that the novel catalyst formed by ionically bonding a transition metal complex to an anion-exchange resin can comprise other complexes and resins than the cobalt porphyrin complex and polystyrene divinylbenzene crosslinked resin exemplified herein, the example having been provided merely to demonstrate practice of the subject invention. Those skilled in the art may readily select other transition metal complexes and resins according to the disclosure made hereinabove. Lastly, although all testing has been done utilizing quadricyclane as the non-conjugated carbon containing compound, other strained cyclic non-conjugated carbon containing compounds may be selected as disclosed hereinabove.

Thus it is believed that any of the variables disclosed herein can readily be determined and controlled without departing from the spirit of the invention herein disclosed and described. Moreover, the scope of the invention shall include all modifications and variations that fall within the scope of the attached claims.

We claim:

1. A process for the photochemical conversion and storage of radiant energy through the conversion of strained cyclic non-conjugated carbon containing compounds to their corresponding conjugated forms comprising the steps of:

adding a catalyst formed by ionically bonding a transition metal complex having a square planar geometry and multiple sites of coordination with an anion-exchange resin to a strained cyclic non-conjugated carbon containing compound; and, converting said non-conjugated carbon containing compound to its corresponding conjugated form with the release of heat energy.

2. The process of claim 1 wherein said square planar geometry of said transition metal complex is provided for by the metal orbital structure of Co.

3. The process of claim 1 wherein said square planar geometry is provided for by a metallophthalocyanine complex.

4. The process of claim 1 wherein said square planar geometry is provided for by a macrocyclic tetraaza complex.

5. The process of claim 1 wherein said strained cyclic non-conjugated carbon containing compound to be converted is quadricyclane.

6. The process of claim 1 wherein said anion-exchange resin is a polystyrene dinvinylbenzene macroporous crosslinked resin.

7. The process of claim 1 wherein said transition metal complex is removed from said anion-exchange resin by using a brine solution.

8. The process of claim 1 wherein said square planar geometry of said transition metal complex is provided for by a porphyrin.

9. The process of claim 8 wherein said transition metal complex is cobalt (II) meso-tetraphenyl porphyrin.

10. The process of claim 1 wherein said square planar geometry of said transition metal complex is provided for by the metal orbital structure of Rh.

11. The process of claim 10 wherein said transition metal complex is chosen from the group consisting of chloronorbornadiene rhodium (I) dimer, tris(dimethylphenylphosphine)norbornadiene rhodium (I) hexafluorophosphate, chlorobis(ethylene)rhodium (I) dimer and chlorodicarbonyl rhodium (I) dimer.

12. The process of claim 1 wherein said square planar geometry of said transition metal complex is provided for by the metal orbital structure of Pd.

13. The process of claim 12 wherein said transition metal complex is dichloro(1,5-cyclooctadiene)palladium (II).

14. The process of claim 1 including the additional steps of:

removing said catalyst;

exposing said conjugated form to radiant energy to reconvert it to its original non-conjugated form; and, re-adding said catalyst which had been removed to said non-conjugated carbon containing compound which had been reconverted from said conjugated form.

15. The process of claim 14 wherein said additional steps are repeated to form a cyclable process.

16. A process for the conversion of strained cyclic non-conjugated carbon containing compounds to strained cyclic conjugated carbon containing compounds comprising the step of:

breaking frangible means of separation between first and second compartment means of a sealed container means, said first compartment providing a catalyst formed by ionically bonding a transition metal complex having a square planar geometry and multiple sites of coordination with an anion-exchange resin and said second compartment means providing a strained cyclic non-conjugated carbon containing compound;

wherein upon interaction between said catalyst and said non-conjugated carbon containing compound, said non-conjugated carbon containing compound is converted to a strained cyclic conjugated carbon containing compound with the release of heat energy.

17. A sealed container means providing reactants for the conversion of strained cyclic non-conjugated carbon containing compounds to strained cyclic conjugated carbon containing compounds comprising:

first compartment means providing a catalyst formed by ionically bonding a transition metal complex having a square planar geometry and multiple sites of coordination with an anion-exchange resin;

second compartment means providing a strained cyclic non-conjugated carbon containing compound; and, frangible means for separating said first and second compartment means from each other.

18. A process for the photochemical conversion and storage of radiant energy comprising the steps of:

exposing a strained cyclic conjugated carbon containing compound to radiant energy which upon exposure is converted to a strained cyclic non-conjugated carbon containing compound;

combining said non-conjugated carbon containing compound with a catalyst formed by ionically bonding a transition metal complex having a square planar geometry and multiple sites of coordination with an anion-exchange resin;

converting said non-conjugated carbon containing compound to said conjugated carbon containing compound with the release of heat energy; and, collecting said heat energy.

19. An apparatus for the photochemical conversion and storage of radiant energy comprising:

container means for storing a strained cyclic conjugated carbon containing compound which, upon exposure to radiant energy is converted to a strained cyclic non-conjugated carbon containing compound;

means for combining said non-conjugated carbon containing compound with a catalyst formed by ionically bonding a transition metal complex having a square planar geometry and multiple sites of coordination with an anion-exchange resin which, upon contact with said non-conjugated carbon containing compound converts non-conjugated carbon containing compound to said conjugated carbon containing compound with the release of heat energy; and, means for collecting said heat energy.

20. The apparatus of claim 19 wherein said means for combining is a heat exchanger means coated with said catalyst.

21. The apparatus of claim 20 wherein said heat exchanger means coated with said catalyst is immersed into said container means.

22. The apparatus of claim 20 wherein said non-conjugated carbon containing compound is transported to said heat exchanger means coated with said catalyst.

* * * * *